(12) United States Patent
Patterson et al.

(10) Patent No.: US 11,318,220 B1
(45) Date of Patent: May 3, 2022

(54) SANITIZING LIGHT FIXTURE FOR DISPLAYING INFORMATION

(71) Applicant: Insight Lighting, Inc., Rio Rancho, NM (US)

(72) Inventors: Jaxon Patterson, Rio Rancho, NM (US); Chris Kreuter, Rio Rancho, NM (US); Geoffry Patterson, Rio Rancho, NM (US)

(73) Assignee: INSIGHT LIGHTING, INC., Rio Rancho, NM (US)

( * ) Notice: Subject to any disclaimer, the term of this patent is extended or adjusted under 35 U.S.C. 154(b) by 109 days.

(21) Appl. No.: 17/025,361

(22) Filed: Sep. 18, 2020

(51) Int. Cl.
*A61L 9/20* (2006.01)
*A61L 2/10* (2006.01)
*F21V 23/00* (2015.01)
*A61L 2/24* (2006.01)

(52) U.S. Cl.
CPC ............... *A61L 9/20* (2013.01); *A61L 2/10* (2013.01); *A61L 2/24* (2013.01); *F21V 23/003* (2013.01); *A61L 2202/14* (2013.01)

(58) Field of Classification Search
None
See application file for complete search history.

(56) References Cited

U.S. PATENT DOCUMENTS

| 10,933,148 | B1 * | 3/2021 | Patterson | ............. F21V 19/001 |
| 2018/0172219 | A1 * | 6/2018 | Van Bommel | ....... A61N 5/0616 |
| 2021/0369905 | A1 * | 12/2021 | Bosua | ....................... A61L 9/20 |

* cited by examiner

*Primary Examiner* — Britt D Hanley
(74) *Attorney, Agent, or Firm* — Rod D. Baker

(57) ABSTRACT

A light fixture devised to provide illuminated sign panes for displaying information to nearby viewers, but including both white light-emitting diodes (LEDs) and UV-C LEDs. The white LEDs are arranged in the fixture so as to illuminate transparent/translucent panes upon which helpful information is displayed, when actuated. The UV-C LEDs also are arranged in the fixture so as to disinfect or sterilize the ambient air near the fixture. The illumination LEDs and the disinfection LEDs are independently switchable "on" and "off," so that a user can controllably illuminate the informational panes, or disinfect the air, or both.

11 Claims, 4 Drawing Sheets

SANITIZING LIGHT FIXTURE FOR DISPLAYING INFORMATION

BACKGROUND OF THE INVENTION

Field of the Invention

This invention relates to light fixtures, particularly to a light fixture for displaying information, such as directional or wayfinding information, and incorporated light-emitting diodes, and specifically to an informational light fixture that illuminates its display and/or emits disinfecting ultraviolet light.

Background

With the increasing concerns regarding contagious diseases that may be transmitted between persons moving about in enclosed public places, it is desirable to disinfect as much as possible the ambient air in such places. It is known that ultraviolet light in the UV-C spectrum can perform sterilizing and disinfecting functions. There is an unmet need for a light fixture that is capable of harnessing electrical power not only to illuminate signage associated with the light fixture, but also (or alternatively) to disinfect the surrounding ambient air with UV-C wavelength light.

SUMMARY OF THE INVENTION

There is disclosed a light fixture devised to provide illuminated sign panes for displaying information to nearby viewers, but distinguished in that it includes both white-light-emitting diodes (LEDs) and UV-C LEDs. The white LEDs are arranged in the fixture so as to illuminate transparent/translucent panes upon which helpful information is displayed, when actuated. The UV-C LEDs also are arranged in the fixture so as to disinfect or sterilize the ambient air that circulates near the fixture. The illumination LEDs and the disinfection LEDs are independently switchable "on" and "off," so that a user can controllably illuminate the informational panes, or disinfect the air, or both.

BRIEF DESCRIPTION OF THE DRAWINGS

The attached drawings, which form part of this disclosure, are as follows.

Like elements are labeled with like numerals in the several views; the drawings are not necessarily to scale, within a view or relative to each other.

DETAILED DESCRIPTION OF THE INVENTION

Figure 1:
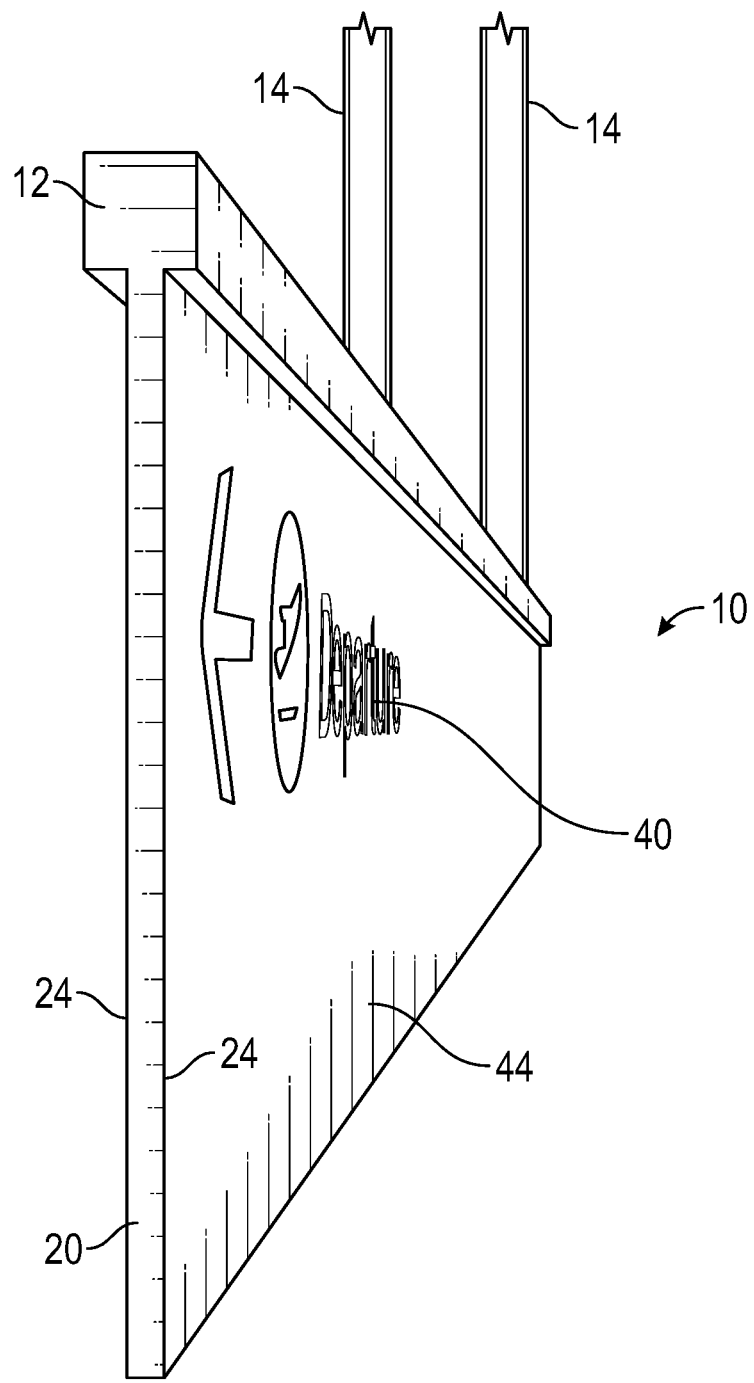
FIG. 1 is a perspective end view of an embodiment of the apparatus according to the present invention.

This invention relates to light fixtures, particularly a light fixture useable for illuminating one or two informational panes, or for both illuminating the pane(s) as well as for disinfecting the ambient air near the fixture. The present light fixture in a preferred embodiment is of an informational type of light fixture suitable for use in commercial buildings, and particularly in buildings where it is desired to display directional and/or advertising information. The disclosed fixture is well-suited for use in, for example, airports, bus stations, commercial shopping malls, train stations, entertainment venues such as motion picture theater complexes, and the like. A fixture according to the present system preferably, but not necessarily, is adapted for installation on the ceiling of a room, corridor, concourse, or hallway, or may be employed in some other overhead context, so to illuminate informational panes which serve as signage viewable by persons in or moving through the corridor or concourse. Such illuminated information sign panes may display directional information to assist persons in plotting movement to a desired location, for example to a particular airport facility (baggage, concourses and gates, ticketing, etc.), or to a particular room or venue in a large complex such as a convention center, casino, courthouse, university building, movie multiplex, etc. Alternatively or simultaneously, the illuminated portions of the fixture may display advertising. Thus, the present system and apparatus include light-emitting diodes (LEDs) to provide beneficial light for illumination purposes.

The light fixture apparatus also employs LEDs to emit sterilizing ultraviolet light to promote disinfection of the air in the room, corridor, hallway, etc., in which the fixture is installed. It is to be understood that while a single fixture apparatus is described herein, a plurality of fixtures may be installed in and/or along a location or venue, connected to an electrical power source by means of wired circuits and switches in compliance with known codes and conventions.

It is desirable in selected contexts, particularly in enclosed buildings where large numbers of persons may congregate or move, to be able to disinfect a location and its ambient environmental air against the presence of microbes, particularly disease-causing pathogens. Pathogens of concern may include but are not necessarily limited to bacteria, viruses, protozoa or fungi. A fixture according to the present disclosure includes light-emitting diodes which emit ultraviolet (UV) light in germicidal wavelengths. UV irradiation is a disinfection method that uses short-wavelength ultraviolet ("ultraviolet C" or UV-C) light to kill or inactivate microorganisms by destroying their nucleic acids, and/or disturbing or disrupting their DNA. A fixture according to the present disclosure accordingly includes LEDs that emit UV-C light. The wavelength of germicidal UV-C is in the range of approximately 100 nanometer (nm) to approximately 280 nm, which wavelengths manifest effective sterilization power. It is known that UV-C exhibits highest germicidal effectiveness at a wavelength of 260 nm±10 nm, which is most effective to kill harmful microorganisms on surfaces in a room. In the present apparatus, therefore, UV-C LEDs are used that emit UV irradiation in wavelength(s) between 100 nm and 280 nm, preferably 260 nm±10 nm.

In the present fixture, UV-C LEDs emit sterilizing wavelengths into the air above the fixture, to sanitize the air as it may later be inhaled by nearby persons (typically pedestrians) in and/or walking through a room or concourse. The air in and about the fixture is warmed, and thus tends to circulate around the fixture; warmed air rises, while treated by the UV-C light, then cools and descends in the vicinity of the fixture to be warmed and recirculated for repeated exposure to the disinfecting UV-C light.

Figure 2:
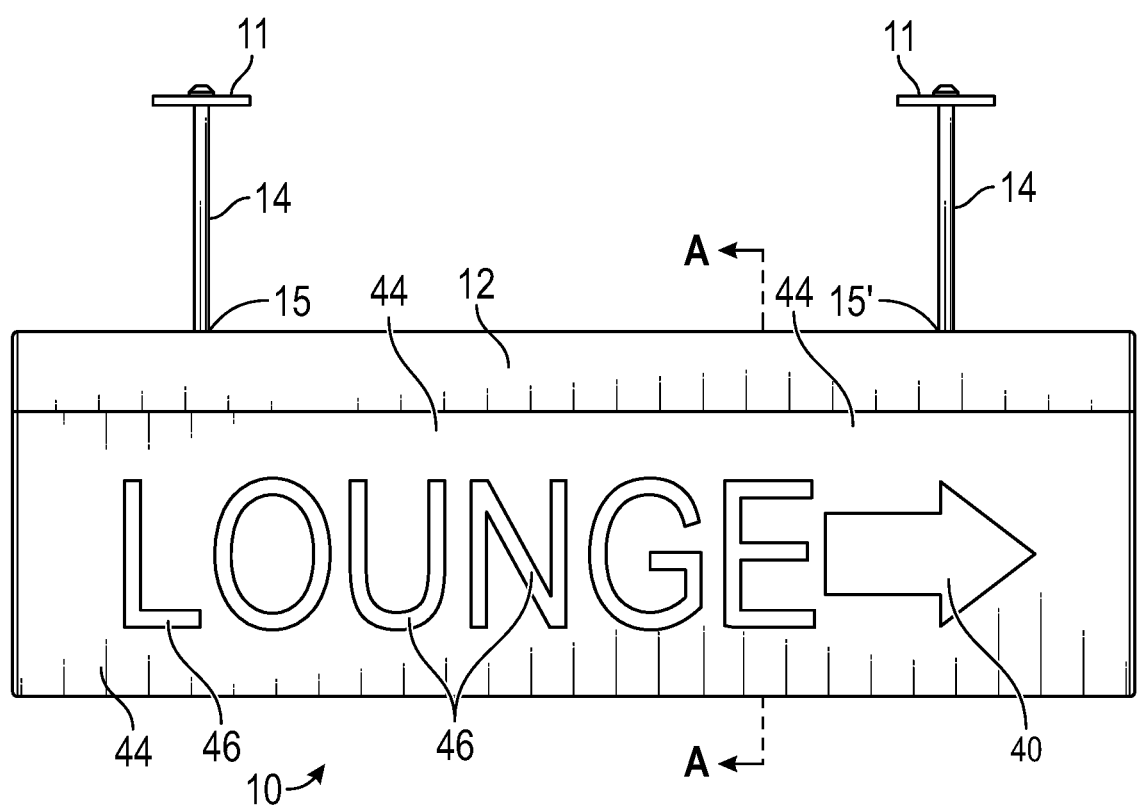
FIG. 2 is a side view of an embodiment of the apparatus according to the present invention.

Attention is invited to FIGS. 1-2 showing an embodiment of the fixture 10 according the present disclosure. The fixture 10 optionally but preferably is adapted to be hung or suspended from an overhead feature such as a ceiling, beam, bracket or the like. Alternative embodiments can be devised to be mounted directly upon or to a supporting surface, so to extend upwardly or laterally from the supporting surface. The fixture 10 includes preferably a hollow elongated housing 12 adapted to be suspended horizontally from the overhead supporting feature 11. At least one, preferably at least two, power suspension cables or conduits 14 are securely attached to the support feature 11 and to the housing 12 to hang the fixture 10. The cables 14 preferably also contain suitable wiring to supply electrical power from the electrical grid or other power source to the fixture 10. A single fixture 10 as seen FIGS. 1 and 2 has a hubs 15, 15' into the housing 12, to which corresponding suspension cables 14 are connected; power is delivered from a cable into at least one of the hubs 15, 15' for powering the electrical components and light source of the fixture 10. The cables 14 can be adapted to any length suitably to locate the fixture 10 an appropriate distance below the support feature 11, and a predetermined selected distance above the flooring or other area in a room or corridor in which the fixture is to be employed.

FIGS. 1 and 2 illustrate that a purpose of the fixture 10 is to provide an illuminated sign, such as a wayfinding or other informational sign. As shall be described further hereafter, a transparent optical panel 20 extends from the housing 12, and there preferably are two translucent support panes 24, 24', upon which signage 40 is provided, also extending from the housing 12 adjacent and substantially parallel to the transparent optical panel 20. Illuminating light rays are emitted from a plurality of illumination light emitting diodes arrayed on a printed circuit board within the housing 12. The illuminating light rays are transmitted from the housing 12 via the transparent optical panel 20 to illuminate the signage provided on the outside faces of the translucent support panes 24, 24'. As shall also be explained further, there is an aperture in the top of the housing 12 through which disinfecting light rays pass upward; the disinfecting light rays are emitted by a plurality of disinfection light emitting diodes arrayed on a printed circuit board within the housing 12.

The housing 12 may be fabricated from extruded aluminum, is hollow to define and enclose an interior space, and may be, by way of example only, about 2.5 inches wide and about 3.5 inches high in overall cross-sectional dimensions. Housing 12 may be, for example, between approximately 24 inches and approximately 96 inches in axial length. The planar transparent optical panel 20, and each planar translucent support pane 24, 24' may be, for example, about 12 inches to 36 inches high, and from about 24 inches to approximately 96 inches long.

Figure 3:
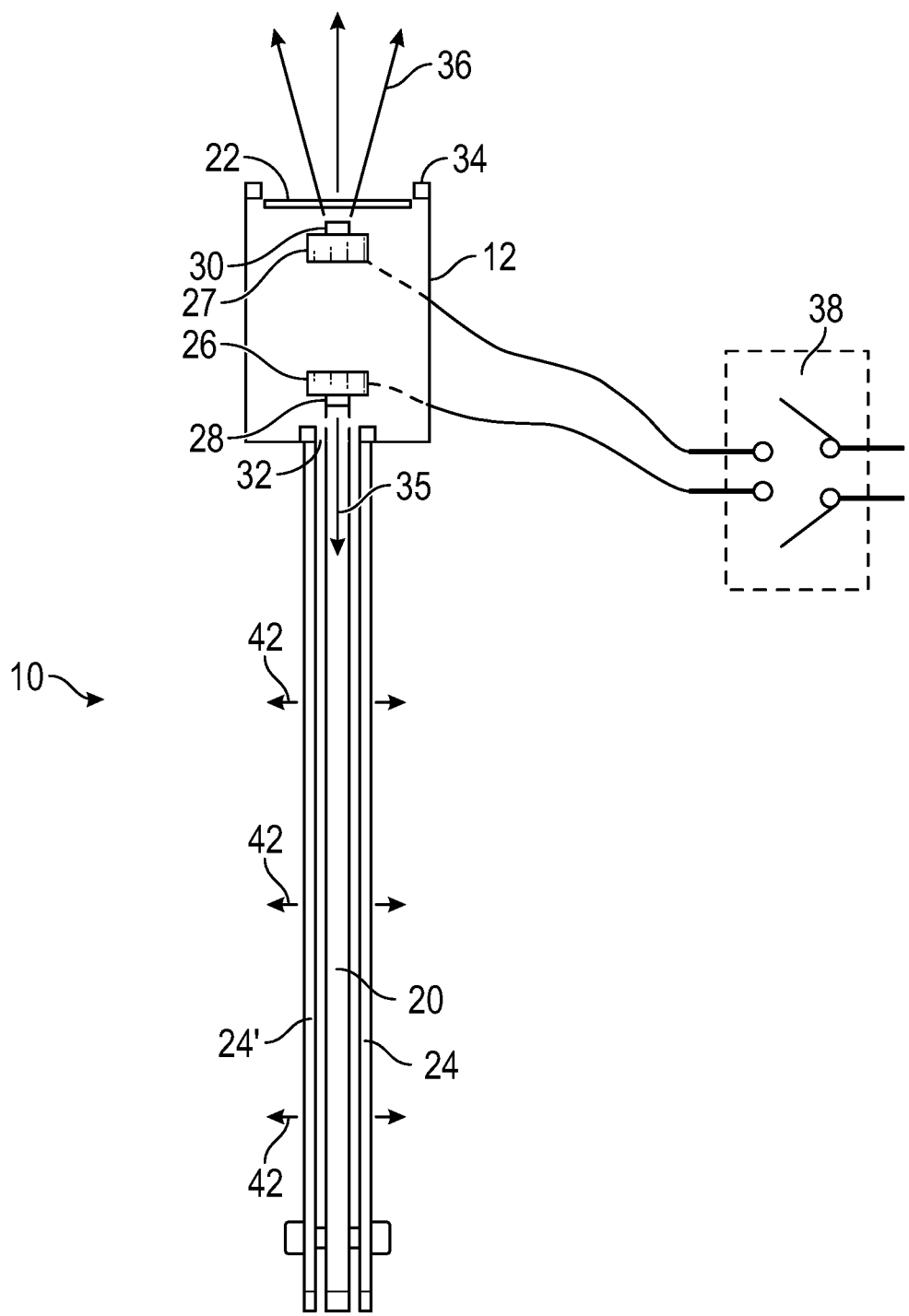
FIG. 3 is a sectional view of the apparatus, taken on section line A-A in FIG. 2.

Combined reference is made to FIGS. 1-3. It is seen, therefore, that according to this disclosure there is provided an informational and sanitizing light fixture 10 that includes the elongated housing 12, the transparent optical panel 20 extending from the housing 12, the at least one, preferably two, translucent support panes 24, 24', upon which signage is disposable, and which extend from the housing 12 adjacent and substantially parallel to the transparent optical panel 20. In a preferred embodiment, the transparent optical panel 20 is manufactured from cast acrylic, and is approximately 8 mm thick and preferably is laser etched. The optical panel 20 serves as the transmission medium for conveying visually illuminating light rays, from illumination light emitting diodes within the housing 12, to the at least one translucent support panes 24, 24', upon which informational signage 40 is disposable. The translucent support panes 24, 24' may be composed of polycarbonate, in sheets between, for example, about 4 mm and about 10 mm thick. Light emanating from the optical panel 20 passes laterally through the at least one translucent support panes 24, 24' to render visible to passersby the informational signage 40.

With particular reference to FIG. 3, there is least one, potentially two, printed circuit boards 26, 27 situated within the housing 12. In a preferred embodiment, a plurality of illumination light emitting diodes 28 are arrayed on a lower printed circuit board 26, while a plurality of disinfection light emitting diodes 30 are arrayed on an upper printed circuit board 27. The disinfection light emitting diodes 30 are provided along most of the length of the fixture housing 12. The disinfection light emitting diodes 30 are light-emitting diodes emitting UV-C light of a wavelength between approximately 100 nanometer (nm) and approximately 280 nm. The illumination light emitting diodes 28 are in positional registration or alignment with a first light aperture 32 in the housing 12, through which aperture 32 pass the visually illuminating light rays 35 (downward directional arrow in FIG. 3) which emanate from within the housing 12 and into the transparent optical panel 20. The illumination light emitting diodes 28 also are provided along most of the length of the fixture housing 12. There also is defined a second light aperture 34 in the housing 12 through which disinfecting light rays 36 (upward directional arrows in FIG. 3) pass to emanate from within the housing. Both apertures 32, 34 are elongated openings that run along nearly the complete length of the housing 12. The second aperture 34 may be closed with a glass cover 22 that feely transmits UV light rays; cover 22 prevents solid debris from entering the housing interior.

Continued reference is invited to FIG. 3. In the preferred embodiment, the first light aperture 32 is defined in the bottom of the housing 12, and the illumination light emitting diodes 28 direct in a downward direction the visually illuminating light rays 35. The transparent optical panel 20 extends downwardly from the housing 12, and is optically coupled with the illumination light emitting diodes 28. It is evident from FIGS. 1 and 3 that, in the preferred embodiment of the fixture 10, the "at least one" translucent support pane includes two translucent support panes 24, 24' extending downwardly from the housing 12 on opposite sides of, and parallelly spaced apart from, the centrally situated optical panel 20.

As seen in FIG. 3, at least one switching assembly 38 is in electrical and operative communication with the circuit boards 26, 27. Switching assembly 38 is the means for turning "on" or "off" the plurality of illumination light emitting diodes 28 and the plurality of disinfection light emitting diodes 30 independently of each other. It is understood, accordingly, that the fixture 10 is operable to emit only disinfecting light rays 36, or only visually illuminating light rays 35, or both disinfecting (36) and visually illuminating (35) light rays.

There thus is provided in operative connection with the fixture 10 and/or its corresponding circuit board(s) 26, 27, the circuit switching means 38 known in the art whereby the visual illumination light emitting diodes 28 and the disinfection light emitting diodes 30 are able to be turned on or off independently. Thus, when it is desired only to illuminate the signage 40 of the fixture 10, an appropriate remotely operated manual switch (e.g. on a wall in a room, or in a master electrical control center) is actuated to activate only the illumination light emitting diodes 28 of the fixture (while leaving the disinfection light emitting diodes 30 off). Alternatively, if it is desired only to disinfect the air in the area, an appropriate switch is actuated to activate only the disinfection light emitting diodes 30 (while leaving the illumination light emitting diodes 28 "off" and dark). Yet further, if and when it is desired to both illuminate and disinfect surfaces in the room, the respective switch(s) of the assembly 38 are operated to activate and "turn on" the visual illumination light emitting diodes 28 and the disinfection light emitting diodes 30. Of course, the switching assembly 38 also can be operated to turn "off" all the LEDs 28, 30 in a room, corridor, or other area. Switching assembly 38 may include a multi-position rotary or rocker switch to permit a user to select between having no LEDs tuned on, all LEDs on, only disinfection LEDs turned on, or only illumination LEDs turned on.

A purpose of the present system and apparatus is to illuminate the signage 40 of the fixture 10. As indicated in FIG. 3, the illumination light emitting diodes 28 arrayed on the printed circuit board 27 emit visually illuminating light rays 35 through the lower light aperture 32 and into upper edge of the transparent optical panel 20 (along most or nearly all the length of the optical panel). As the transparent optical panel 20 extends downwardly from the housing 12, it is optically coupled with the illumination light emitting diodes 28. Thus, the illuminating light rays 35 enter the top edge optical panel 20 and are transmitted through the height of the panel 20, but also are diffusively emitted laterally through the translucent support panes 24, 24' and outward from the faces of the support panes. The lateral emission of illumination light rays is suggested by the sideways directed arrows 42 of FIG. 3.

FIGS. 1 and 2, illustrate that a signage 40, which can be nearly any type or content of information, is presented on the outside faces of the translucent support panes 24, 24'. The signage 40 is illuminated by the visible light rays 42 that pass outwardly through the support panes, and then are affected by a thin layer of material 44 on the outside faces of the support panes 24, 24'. Signage 40 may preferably be illuminated in either of two ways. In one manner, the signage 40 has a thin layer 44 that is translucent (e.g., a thin layer of applied plastic/polymer, a pigment, paint, or dye, or a thin fabric, etc.). The translucent thin layer 44 is applied to the outside surface of each support pane 24, 24'. The informational data, such as graphics, alpha-numerics, etc., are embedded or embodied in, or composed on, the thin translucent layer 44. The passage of the visible light rays 42 through the thin layer causes the signage 40 information to be visibly illuminated for viewing by persons seeing the fixture 10. Alternatively, the thin layer 44 may be composed of a material opaque to the transmission of visible light, in which case informational data (again, e.g., graphics, alpha-numerics, etc.) may be defined by designed portions of the layer 44 that are cut-out, removed, or otherwise absent/omitted from the layer 44. In this embodiment, the visible light rays 42 are blocked by the thin layer 44, but pass through the defined cut-out portions 46. The signage 40 is viewable as the rays 42 which emanate from the openings 46 through the opaque thin layer 44.

Accordingly in one preferred embodiment, the thin layer 44 of the signage is a vinyl layer adhered to at least one of the translucent support panes 24, 24'. The vinyl layer 44 may be opaque, and defines at least one shaped aperture 46 therein, wherein the illuminating light rays 42 are emitted from a translucent pane 24 or 24' through the at least one shaped aperture to present viewable information. Alternatively, the vinyl layer is translucent and has viewable information disposed, as by printing or the like, thereon.

Referring again to FIGS. 1-3, it is seen that the fixture 10 serves to sterilize the ambient air above the housing 12, for example in the space between the housing and the ceiling or other support feature 11. When the disinfection light emitting diodes 30 are activated, sanitizing UV light passes through the ambient air to help kill undesirable microbes that may be dispersed and suspended in the vicinity above the housing 12. As is apparent from previous discussion, the second light aperture 34 is defined in the top of the housing 12, so that the disinfection light emitting diodes 30 can direct the disinfecting light rays 36 upwardly through the second light aperture and into the space above the housing.

Figure 4:
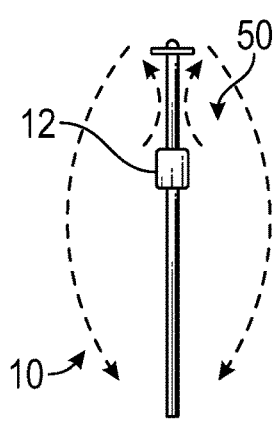
FIG. 4 is an end view of an apparatus according to the present invention, diagrammatically depicting a beneficial recirculating flow of ambient air around the apparatus.
Figure 5:
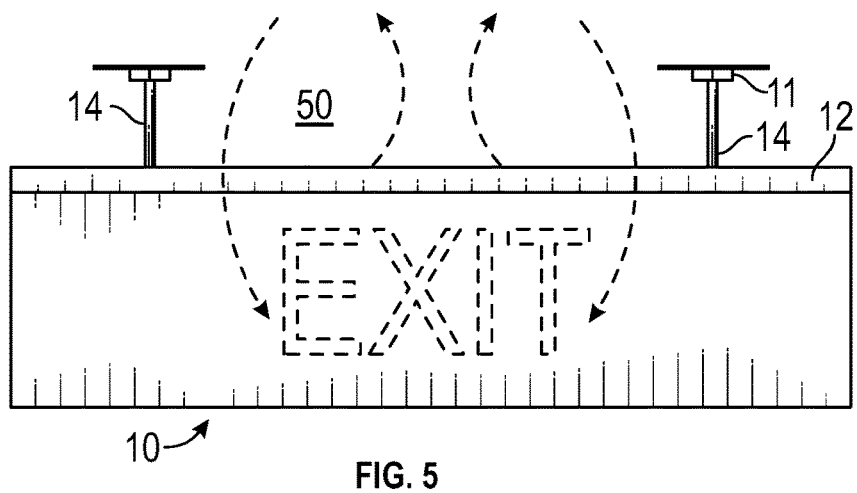
FIG. 5 is a side view of the apparatus of FIG. 4, diagrammatically depicting a recirculating flow of ambient air around the apparatus.

FIGS. 4 and 5 illustrate diagrammatically an advantageous feature and function of the inventive fixture 10. It is well-known that warmed air rises, and if it cools it then falls or descends. The invention exploits this principle of physics to circulate the ambient air about the fixture 10. The dashed directional arrows shown in the figures illustrate a recirculating air flow around the fixture 10. Ambient air nearby the sides of the fixture 10 is warmed by heat generated by the fixture 10 (in addition to any other heating agents in the environmental vicinity). The warmer air rises to and through the vicinity of the fixture 10, and particularly to and into the upper-more volumes in the space 50 above the housing 12, as indicated by the curved upwardly directed dashed arrows of FIG. 4-5. Upon reaching and occupying the space 50, the air is treated by the sterilizing effect of the disinfecting light rays 36 continuously passing through the treatment space 50. While temporarily residing in the space 50, the moving air is decontaminated and further warmed. The warmed, decontaminated air rises further to exit the space 50 and then cools. The cooled, decontaminated air then descends downward, as indicated by the curved downwardly directed dashed arrows of FIG. 4-5. Some of the cooled, and at least partially sterilized, air freely descends down past the fixture 10 into the areas below the fixture, thereby providing improved air quality to persons passing through areas beneath the fixture 10. Some other fraction of the cooled descending air may be warmed by its passage past the fixture 10, whereby it then rises upward again to the treatment space 50 above the housing 50, and the cycle is then repeated.

Although the invention has been described in detail with particular reference to these preferred embodiments, other embodiments can achieve the same results. In this description, specific details are set forth, such as specific materials, structures, processes, etc., in order to provide a thorough understanding of the present invention. However, as one having ordinary skill in the art of light fixture construction would recognize, the present invention can be practiced without resorting strictly only to the details specifically set forth. In other instances, well-known concepts and compositions have not been described in detail, in order not to unnecessarily obscure the present invention.

Only some embodiments of the invention and but a few examples of its versatility are described in the present disclosure. It is understood that the invention is capable of use in various other combinations and is capable of changes or modifications within the scope of the inventive concept as expressed herein. Modifications of the invention will be obvious to those skilled in the art and it is intended to cover with the appended claims all such modifications and equivalents.

What is claimed is:

1. A combination informational and sanitizing light fixture comprising:
   an elongated housing;
   a transparent optical panel extending from the housing;
   at least one translucent support pane, upon which signage is disposed, extending from the housing adjacent and substantially parallel to the transparent optical panel;
   at least one printed circuit board situated in the housing;
   a plurality of visible illumination light emitting diodes arrayed on the printed circuit board;
   a plurality of disinfecting UV-C light emitting diodes arrayed on the printed circuit board;
   a first light aperture in the housing through which pass visually illuminating light rays emanate from within the housing and into the transparent panel;
   a second light aperture in the housing through which disinfecting light rays emanate from within the housing;
   at least one switch for turning on or off the plurality of visible illumination light emitting diodes and the plurality of disinfecting UV-C light emitting diodes independently of each other;
   wherein the fixture is operable to emit only disinfecting light rays, or only visually illuminating light rays, or both disinfecting and visually illuminating light rays.

2. The fixture according to claim 1 wherein the elongated housing is adapted to be suspended horizontally.

3. The fixture according to claim 2 wherein:
   the first light aperture is defined in the bottom of the housing;
   the visible illumination light emitting diodes direct downward the visually illuminating light rays; and
   the transparent optical panel extends downwardly from the housing, and is optically coupled with the visible illumination light emitting diodes.

4. The fixture according to claim 3 wherein the transparent optical panel comprises cast acrylic.

5. The fixture according to claim 2 wherein the at least one translucent support pane comprises two translucent support panes extending downwardly from the housing on opposite sides of, and parallelly spaced apart from, the optical panel.

6. The fixture according to claim 5 wherein the translucent support panes comprise polycarbonate.

7. The fixture according to claim 3 wherein the signage comprises a vinyl layer adhered to the at least one translucent support pane.

8. The fixture according to claim 7 wherein the vinyl layer is opaque and defines at least one shaped aperture therein, and wherein further the visually illuminating light rays are emitted from the transparent panel through the at least one shaped aperture to present viewable information.

9. The fixture according to claim 7 wherein the vinyl layer is translucent and has viewable information disposed thereon.

10. The fixture according to claim 2 wherein the second tight aperture is defined in the top of the housing, and the disinfecting UV-C light emitting diodes direct the disinfecting light rays upwardly through the second light aperture.

11. The fixture according to claim 1 wherein the plurality of disinfecting UV-C light emitting diodes comprise diodes emitting UV-C light of a wavelength between approximately 100 nanometer (nm) and approximately 280 nm.

* * * * *